United States Patent [19]

Strobel et al.

[11] Patent Number: 5,445,809
[45] Date of Patent: Aug. 29, 1995

[54] PRODUCTION OF TAXOL FROM THE YEW TREE

[75] Inventors: Gary A. Strobel, Bozeman; Andrea A. Stierle, Butte, both of Mont.

[73] Assignee: Research and Development Institute at Montana State University, Bozeman, Mont.

[21] Appl. No.: 970,887

[22] Filed: Nov. 3, 1992

Related U.S. Application Data

[63] Continuation-in-part of Ser. No. 845,097, Mar. 3, 1992.

[51] Int. Cl.⁶ .................... A61K 51/00; C07D 305/00
[52] U.S. Cl. ..................................... 424/1.81; 549/510
[58] Field of Search ................. 549/510; 424/1.1, 1.81

[56] References Cited

U.S. PATENT DOCUMENTS

| | | | |
|---|---|---|---|
| Re. 34,277 | 6/1993 | Denis et al. | 549/510 |
| 4,049,683 | 9/1977 | Okamoto et al. | 424/1.81 X |
| 4,206,221 | 6/1980 | Miller et al. | 549/510 |
| 4,814,470 | 3/1989 | Colin et al. | 549/510 X |
| 4,857,653 | 8/1989 | Colin et al. | 549/510 X |
| 4,924,011 | 5/1990 | Denis et al. | 549/510 |
| 4,942,184 | 7/1990 | Haugwitz et al. | 514/449 |
| 4,960,815 | 10/1990 | Moos | 424/1.81 |
| 5,019,504 | 5/1991 | Christen et al. | 435/123 |
| 5,202,448 | 4/1993 | Carver et al. | 549/510 |
| 5,232,684 | 8/1993 | Blumberg et al. | 424/1.1 |
| 5,243,045 | 9/1993 | Holton et al. | 544/60 |
| 5,312,740 | 5/1994 | Saito et al. | 435/123 |

OTHER PUBLICATIONS

M. C. Wani et al., "Journal of the American Chemical Society", vol. 93, No. 9, pp. 2325–2327, May 1971.

Parness et al., *J. Cell. Biol.*, vol. 91 (Nov. 1981) pp. 478–487.

Chenu et al., *Journal of Labelled Compounds and Radiopharmaceuticals*, vol. 24, No. 10 (1987) "Synthesis of a [3H]-Labelled Derivative of the Microtubular POison Taxol", pp. 1245–1255.

*Primary Examiner*—Gary L. Geist
*Assistant Examiner*—Lara E. Chapman
*Attorney, Agent, or Firm*—Lowe, Price, LeBlanc & Becker

[57] ABSTRACT

Taxol and radiolabelled taxol are produced from sterilized Yew trees by contacting sterilized Yew tree stock with a reactor solution comprising a taxol precursor under a reducing environment. The reactor solution may also contain a reducing agent, an energy source, a buffer to maintain pH in the range of 6.0 to 8.0, and a steroid inhibitor. A radiolabelled precursor may be included in the reactor solution to produced radiolabelled taxol.

22 Claims, 6 Drawing Sheets

PRODUCTION OF TAXOL FROM THE YEW TREE

This is a continuation-in-part of U.S. application Ser. No. 07/845,097, filed Mar. 3, 1992, now pending.

FIELD OF THE INVENTION

This invention relates to a method for the production of taxol, and more particularly to a method to produce taxol from the Yew tree at substantially improved levels.

BACKGROUND OF THE INVENTION

Taxol, which is of the chemical structural formula:

shows significant properties of promoting the polymerization of tubulin and inhibiting the depolymerization of microtubules. For these reasons, taxol is a valuable antileukemia and antitumor agent and is the subject of increasing research.

Taxol is known to be extracted from the trunk bark of different species of the Taxus, or Yew tree. Yields are generally low, usually on the order of no more than about 100 milligrams per kilogram in the extraction process. Various procedures for the production of taxol are known for example, from U.S. Pat. Nos. 4,814,470 and 4,857,653. A chemical process for the preparation of taxol is disclosed in U.S. Pat. No. 4,924,011.

Wani et al, "Journal of the American Chemical society", Vol. 93, May 1971, No. 9, pages 2325–2327, reports on the structure of taxol and its potential use as an antileukemic and tumor inhibitory compound. This publication further discusses an alcohol extraction procedure for obtaining taxol from the stem bark of the western Yew tree (*Taxus brevifolia*).

The present invention provides a new method for the production of increased quantities of taxol and radiolabelled taxol using a novel procedure.

SUMMARY OF THE INVENTION

It is accordingly one object of the present invention to provide a new method for the production of taxol in substantial quantities.

A further object of the invention is to provide a method for the production of taxol from Yew tree stock by a novel procedure which utilizes a combination of reagents to synthesize and produce taxol.

A further object of the invention is to provide novel taxol derivatives and methods for use.

Other objects and advantages of the invention will become apparent as the description thereof proceeds.

In satisfaction of the foregoing objects and advantages, the present invention provides a method for the production of taxol from a Yew tree which comprises:

a. providing a taxol production source comprising at least a portion of a Yew tree;

b. contacting said taxol production source with a reactor solution comprising one or more of the following reagents:
 1. a reducing agent;
 2. a taxol precursor; or
 3. asteroid inhibitor; said solution being maintained at a pH in the range of about 6.0 to 8.0; and c. maintaining contact of said portion of said taxol production source with said reactor solution, for a sufficient time to produce taxol.

In a further embodiment of the invention, there is provided a radioactive labelled taxol product and methods for use of the radioactive labelled taxol.

BRIEF DESCRIPTION OF DRAWINGS

Reference is now made to the drawings accompanying this application, wherein.

DESCRIPTION OF THE INVENTION

This invention is concerned with a method for the production of taxol and novel taxol derivatives. As mentioned above, taxol is a known valuable antileukemia and antitumor agent, which has been extracted from trunk barks of different species of Taxus or Yew trees. Taxol is of the following structural formula:

There have been substantial difficulties in the art in obtaining sufficient quantities of taxol to fully explore the potential antileukemia and antitumor properties. The known methods for production of taxol are extraction processes which isolate small amounts from various species of the Taxus or Yew tree, primarily from the bark of such trees.

The present invention provides a new method which produces taxol at a level three to five times greater than which is extractable by methods known to the art. The method of the invention produces taxol through a combination extraction and synthesis procedure to provide high levels of taxol from various parts of the Taxus or Yew tree.

An advantage of the method of the present invention is that it is useful with any portion of the Yew tree which can serve as a source of taxol, a taxol derivative, or a taxol precursor. Thus, the method utilizes the bark (both inner and outer), sapwood (both old growth and new growth), roots, limbs, twigs, needles or any other plant part which can be used to make taxol.

The method is also applicable to other Yew species such as *Taxus baccata, Taxus cuspiduta, Taxus canadensis,* or *Taxus floridana*. The method of the invention is also considered applicable to any other plant or tree or other source which could serve as a source of taxol in the method of the invention.

The present invention is directed to a method for the production of taxol and not merely extraction of taxol from the Yew tree, as in prior art processes. According to this invention, the reactor solution includes a taxol precursor, which with other reagents contained in the reactor solution enables the synthesis of taxol. The taxol precursor is any chemical reagent which contains any of the basic building blocks of the taxol compound. As described herein, especially suitable taxol precursors are those which contain acyl radicals such as acetic acid or corresponding esters, as well as compounds which contain amino acid radicals and benzene rings. The taxol precursors thus include organic compounds which contain one or more acyl radicals including carboxylic acids and the corresponding acyl halides, esters, or salts, amino acids including peptides, lactones and combinations thereof. Any compound which can act as a taxol precursor is considered to be useful and suitable for the process of the invention. Particularly preferred are benzoic acid precursors, derivatives, or salt, such as sodium benzoate.

As discussed herein, the reactor solution also preferably includes a reducing agent to maintain a reducing atmosphere during the reaction. The reactor solution may also contain a source of energy such as a sugar, a buffering agent to maintain the appropriate pH in the system, and optionally, vitamins and minerals. Asteroid inhibitor to block formation of undesirable lipoidal substances and improve yields is also helpful. All of the reactor components are maintained in aqueous solution, highly preferably, a sterile water solution.

The chemical reactions which occur during the method for production of taxol according to this invention are not completely understood. However, it is believed that one or more components of the reactor solution react with taxol precursors contained in the Yew tree to produce the taxol.

It is also an important feature of the invention that the pieces of Yew tree be aseptic for best results. The presence of various types of microorganisms and fungi which are often found on trees may interfere with the reaction and should be destroyed by disinfecting the tree or tree parts prior to use in the process.

It is also a feature of the invention that the process can be run on a continuous basis. The continuous process is conducted by replacement of the reactor solution on a regular basis such as daily by the addition of fresh reactor solution. With careful control of the process, taxol than can be produced on a daily basis over a substantial period of time to provide greater quantities of taxol than previously possible.

A preferred aspect of the present invention is a continuous process wherein either appropriate fresh nutrients are added to the reaction solution to supplement and maintain the production of taxol, or the reaction medium is exchanged for a fresh medium solution on a regular basis.

It is a further feature of the invention that labelled taxol can be produced by use of a labelled precursor as described herein. Radiolabelled taxol is a new compound, and because of the radiolabel, it and its derivatives can be identified in the mammal body so one can determine how taxol functions as an antileukemia and antitumor agent. The taxol may be labelled with any label (stable or unstable) including $^{14}C$, $^{13}C$, tritium ($^{3}H$) or $^{15}N$.

The labelled taxol can be easily recovered from the reactor at various SP activities depending on the precursor used and the specific activity of the precursor. The labeling of taxol can also be specifically determined depending on which precursor is used and the relative location of the label present. NaAc-1-$^{14}C$ appears at present to be the best precursor for obtaining universally labelled $^{14}C$ taxol. The following Table 1 shows the location of the $^{14}C$ label in taxol as a function of $^{14}C$ precursor in an in vitro system using five different compound precursors.

TABLE 1

| Compound precursor | Base hydrolysis % in aqueous | Base hydrolysis % in chloroform | % acid volatile |
|---|---|---|---|
| Sodium acetate-1-$^{14}C$ | 66 | 34 | 35 |
| Mevalonolactone-2-$^{14}C$ | 92 | 8 | 18 |
| Glucose-UL-$^{14}C$ | 91 | 9 | 61 |
| Leucine-1-$^{14}C$ | 79 | 21 | 0 |
| Phenylalanine-UL-$^{14}C$ | 76 | 24 | 0 |

Location of $^{14}C$ in taxol as a function of $^{14}C$ precursor in the in vitro system In the method of the invention, taxol is produced from Yew tree stock by mixing a portion of the Yew tree stock with a reactor solution of a specialized nature. The Yew tree portion can be bark, needles or any other plant part which produces taxol, and preferably is freshly cut material. However, Yew logs which have been stored under high humidity levels and relatively low temperatures, are also acceptable. Storage at about 4° C. and about 90–95% relative humidity are satisfactory. The yew logs continue to be taxol productive for 6 months or more.

Figures 1, 1A:
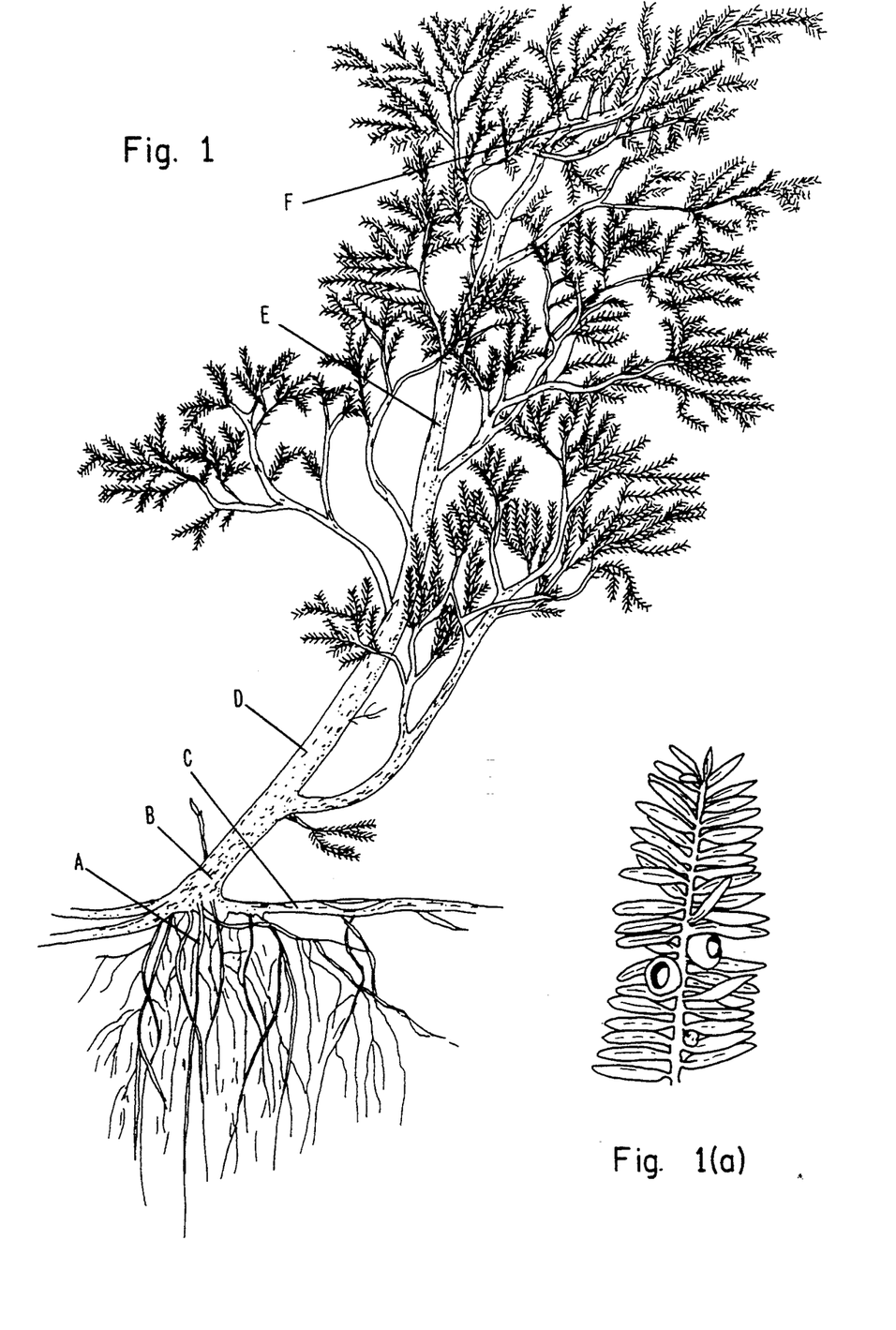
FIG. 1 is a diagram of a Yew tree in which areas are designated which have the greatest taxol synthesizing ability (B, C, D)

The portion of the Yew tree which produces the most taxol is illustrated in FIG. 1, wherein (A) is the vertical roots of the Yew tree, (B) is the base of the Yew tree, (C) is a lower lateral stem of the Yew tree, (D) is the lower main trunk of the Yew tree, (E) is the upper main trunk and (F) designates the top trunk of the Yew tree. It has been discovered that the portion of the tree which produces the most taxol is the portion indicated as D, preferably that portion located at the base of the tree about one to two meters from ground level of a seven meter tree. In other words, the lower 20% of the trunk of the tree represents the preferred source of the taxol synthesizing ability.

In preparing the bark, needles or any other plant part for treatment according to this invention, it is preferred to provide logs of the tree of about two to three feet in length which are then treated or sprayed with a disinfectant to kill indigenous surface organisms. An alcohol solution is satisfactory, preferably a 70 wt. % ethanol-water solution. The disinfectant should then be allowed to dry. Subsequently, all physical materials which will contact the log surface such as knives, gloves or hands should also be disinfected or sterilized prior to working with the wood pieces.

In a preferred procedure, the outer bark of the log is removed so the inner bark can be obtained. Preferably the inner bark and outer bark are removed as strips which are then cut into size as desired. Sterilized shears should be used for cutting. After recovery, the bark pieces obtained should be quickly (within 1–3 minutes) placed into the reactor solution to prevent drying and oxidation of the inner bark. The process should be repeated several times to provide sufficient bark to operate the reactor.

Figure 2:
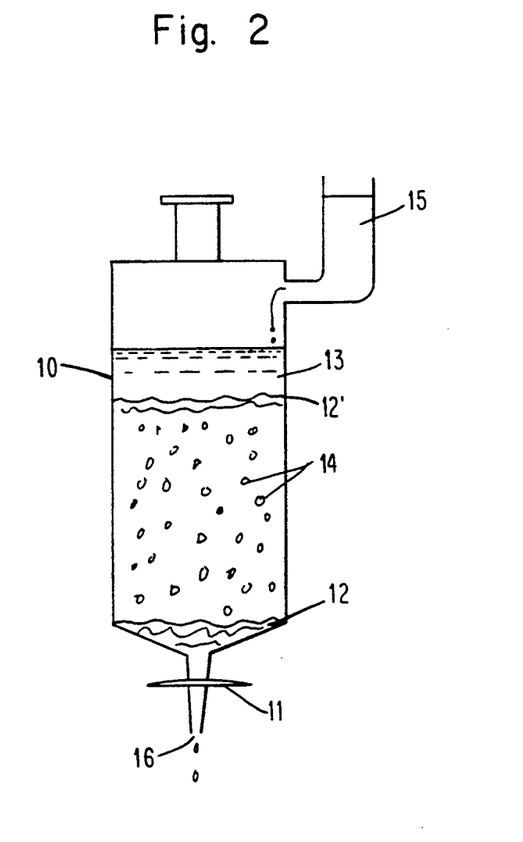
FIG. 2 is a reactor for conducting the process of the invention.

A preferred but small volume reactor is shown in the sketch of FIG. 2. As shown in FIG. 2, the reactor is preferably a glass tube 10 having a stopcock 11 at the base. Sterile glass wool 12 and 12' are preferably maintained in the base of the reactor and at the top of the reactor to keep the pieces of bark or Yew tree submerged in the liquid. The reactor solution 13 contains bark or other wood pieces 14. The reactor is provided with an inlet 15 for addition of fresh reactor fluid and used reactor fluid is removed from the reactor by stopcock 11 through exit 16. The reactor should be provided with conventional means to heat the reactor contents.

The reactor solution contains several essential components. An essential ingredient of the solution is a taxol precursor, that is, a material which can serve as an essential element of the taxol to be produced. Acetic acid, other source of acyl radical, or corresponding ester derivatives, e.g., acetates, may be used. Esters and salts may also be used. Compounds which contain benzene rings are suitable, e.g., benzene, benzoic acid, a benzoic acid derivative or a benzoic acid salt. Amino acids such as phenylalanine, leucine, and the like, are especially satisfactory since the chemical structures of amino acids form at least a portion of the taxol chemical structure. Lactones and combinations of these precursors may be used. One or more precursors may be present at various concentrations. If an amino acid is not used as a precursor, than a nitrogen source (about 0.1 to 20 mM) should also be included in the reactor solution since benzene and acyl radicals do not contain nitrogen, which is essential to the taxol structure. Preferred nitrogen sources are nitrates, $NH_4$ and amines.

A reducing agent is useful to provide a reducing environment in the reactor solution. The reducing agent precludes oxidation of the tissue of the wood which would cause production of oxidation products such as quinones and cause the reaction to cease. Preferred reducing agents are dithiothreitol, ascorbic acid or mercaptoethanol although any effective reducing agent may be used. There should be sufficient reducing agent in the solution to preclude oxidation. About 5 to 15 mM is generally sufficient.

A further useful ingredient of the reactor solution is an energy source in sufficient concentration (usually about 1 mM to 10 mM should be sufficient) to maintain tissue integrity and life of the solution. A sugar compound is preferable such as glucose, sucrose, mannose, galactose, fructose or mixtures thereof, other sugar equivalents or any other sugar derivative.

It is a preferred aspect of this invention that the taxol precursor be present as a labelled material, so that the resulting taxol produced will be radiolabelled. The taxol precursor is preferably labelled with a radioactive carbon. Tritium ($^3H$) and $^{14}C$ are preferred. Preferred labeled precursors are $^{14}C$ glucose, $^{14}C$ sucrose, $^{14}C$ phenylalanine, or $^{14}C$ mevalonolactone. Equivalent materials may be used.

A further useful, but optional component of the reactor solution is a steroid inhibitor such as chlorocholine chloride, fungal elicitors, or gibberellic acid $A_3$. The steroid inhibitor is present basically as a metabolic blocker to force the reaction toward production of taxol and prevent production of analogous materials such as lipids. The steroid inhibitor is present in amounts of about 0.16 to 1.6 mM.

While optional, best results are obtained if vitamins and minerals are also present in the reactor solution. Vitamins such as acetyl CoA, biotin, niacin, and $B_6$ are useful. Acetyl CoA is useful in the process. Minerals may also be present in the reactor solution such as $Fe^{+++}$, Mg, Mn, Ca or K.

There should also be present in the reactor solution sufficient buffering agents to maintain a pH in the reactor solution in the range of 6.0 to 8.0, preferably 6.5 to 7.5 and preferably 7.0. Any suitable buffer may be used; however potassium hydrogen phosphate and potassium dihydrogen phosphate are satisfactory. Buffers can be used in concentrations of about 0.5 to 5 mM.

In conducting the synthesis of this invention, the components of the reactor solution are dissolved in water, preferably sterilized water. The reactor components and the pieces of Yew tree are placed into the sterile aqueous solution. In general, the solution should contain about 0.4 grams of plant material for each 2 ml of water. The remaining essential ingredients of the reactor solution are then added in the indicated amounts and the reaction begun.

The temperature of the reaction should range from 25°–30° C., with a preferred temperature of 27° C. Heating is done conventionally. Atmospheric pressure is satisfactory.

It is a feature of the invention that the process is a sustaining process. Thus, taxol can be continuously produced with the addition of fresh reactor solution on a regular basis, such as daily. The reactor solution is changed by draining and replacing quickly with an equivalent amount of replacement reactor solution. The yew pieces are left intact in the reactor while only the reactor solution is changed. Alternatively, nutrients can be added to the solution. Optionally, the solution is filtered, any undesired waste products removed, and the filtered solution returned to the reaction medium. The filtered solution or the reaction medium is supplemented to provide any desired nutrients which have been used. Maximum production of taxol can be maintained by monitoring the solution to provide the necessary nutrients in optimum proportions.

In conducting the reaction, the conditions for best results require that yew inner bark from the base of the Yew tree be utilized in sterilized form as the starting material. As pointed out above, various other parts of the Yew tree can be used but the inner bark from the base of the tree provides best results.

The temperature of the incubation should be in the range of 25–30° C., preferably about 27° C., and the reactor solution should be changed daily. It is essential that the reactor solution contain a taxol precursor and a reducing environment be maintained. Best results are obtained if all pieces of the Yew tree are submerged in the solution.

The radiolabelled taxol produced according to the present invention can also be provided as a pharmaceutical composition in combination with one or more pharmaceutically acceptable inert or physiologically active diluents or adjuvants. These compositions may be prepared in any form appropriate for the administration route desired. The parenteral route and especially the intravenous route are preferred methods of administration. Compositions for parenteral adminstration may be aqueous or nonaqueous sterile solutions, suspension or emulsions. Propylene glycol, vegetable oils, injectable organic esters and the like, may be used as solvents or vehicles. The compositions may also contain adjuvants, wetting agents emulsifiers or dispersants. The compositions may also be in the form of sterile solid solutions which may be dissolved or dispersed in sterile water or any other injectable sterile medium. The pharmaceutical compositions may be particularly used in the treatment of acute leukemia and solid tumors at doses known to the art, but generally in the range of between one and two milligrams per kilograms of by weight by the intravenous route for an adult. The pharmaceutical compositions should contain about 0.01 to 1.0 wt. % of effective ingredient.

The following examples are presented to illustrate the invention but it is not to be considered as limited thereto. In the examples, and throughout the specification, parts are by weight unless otherwise indicated.

EXAMPLE 1

Utilization of Yew Wood Inner Bark in the Reactor

In this example, a reactor as exemplified in FIG. 2 was utilized. The yew wood provided was from basal logs two to three feet in length from the base of a Yew tree one to two meters from ground level. The logs were treated with a solution of 70% ethanol to kill indigenous surface organisms. All knives and lab surfaces were treated with 70% ethanol in preparation for the experiment and sterile gloves were used. In preparing the pieces of the log, the outer bark was removed on an area 6 cm wide and 15-20 cm long. The inner bark was then cut from the log in pieces 1-2 cm wide and 15-20 cm long. These strips were then cut into 5 mm×5 mm pieces with sterilized scissors. The pieces were quickly placed into the reactor solution to prevent drying and oxidation of the inner bark which could occur within one to two minutes. This process was repeated several times to provide the bark needed for the reactor.

A reactor solution in sterile water was prepared as follows:
1. 10 mM Dithiothreitol;
2. 1 mM Glucose;
3. 1 mM Potassium dihydrogen phosphate and dipotassium hydrogen phosphate to maintain pH at 7.0;
4. 20 mM Phenylalanine and 15 µCi NaAc-1-$^{14}$C; and
5. 0.16 mM Steroid inhibitor, chlorocholine chloride.

In the reactor, there were 0.4 grams of yew bark for each 2 mm of water.

The reactor was started using 10 grams of inner bark pieces and 30 ml of reactor solution. The reactor was drained daily and quickly replaced with 20 ml of replacement solution having the same composition as described. A sample of 5 ml of each daily reactor solution was extracted with 5 ml of chloroform. The chloroform extract was chromatographed on thin layer chromatography with standard taxol as a reference standard. The band (Rf 0.67) was cut out of the plate and eluted with acetonitrile and taxol estimated at 273 angstroms (E=1700). Radioactivity in this sample was also determined by liquid scintillation counting.

Figure 3:
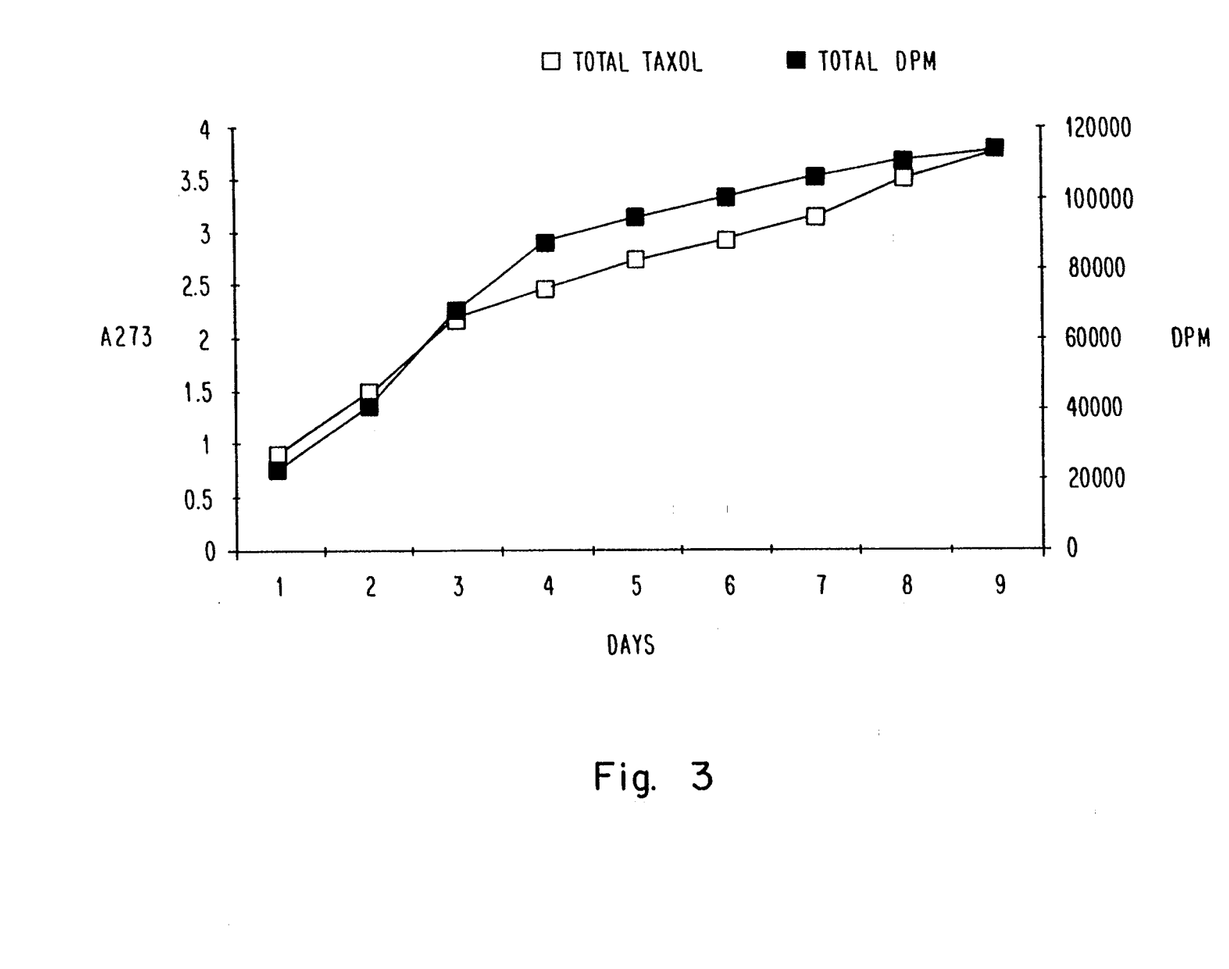
FIG. 3 is a graph illustrating the cumulative production of taxol by the method of the invention.

From this experiment, it was clear that de novo production of taxol occurred as shown in FIG. 3, as measured by the incorporation of $^{14}$C from the acetate $^{14}$C precursor. As shown in FIG. 3, the amount of taxol produced increased up to day nine and continued to increase.

Figure 4:
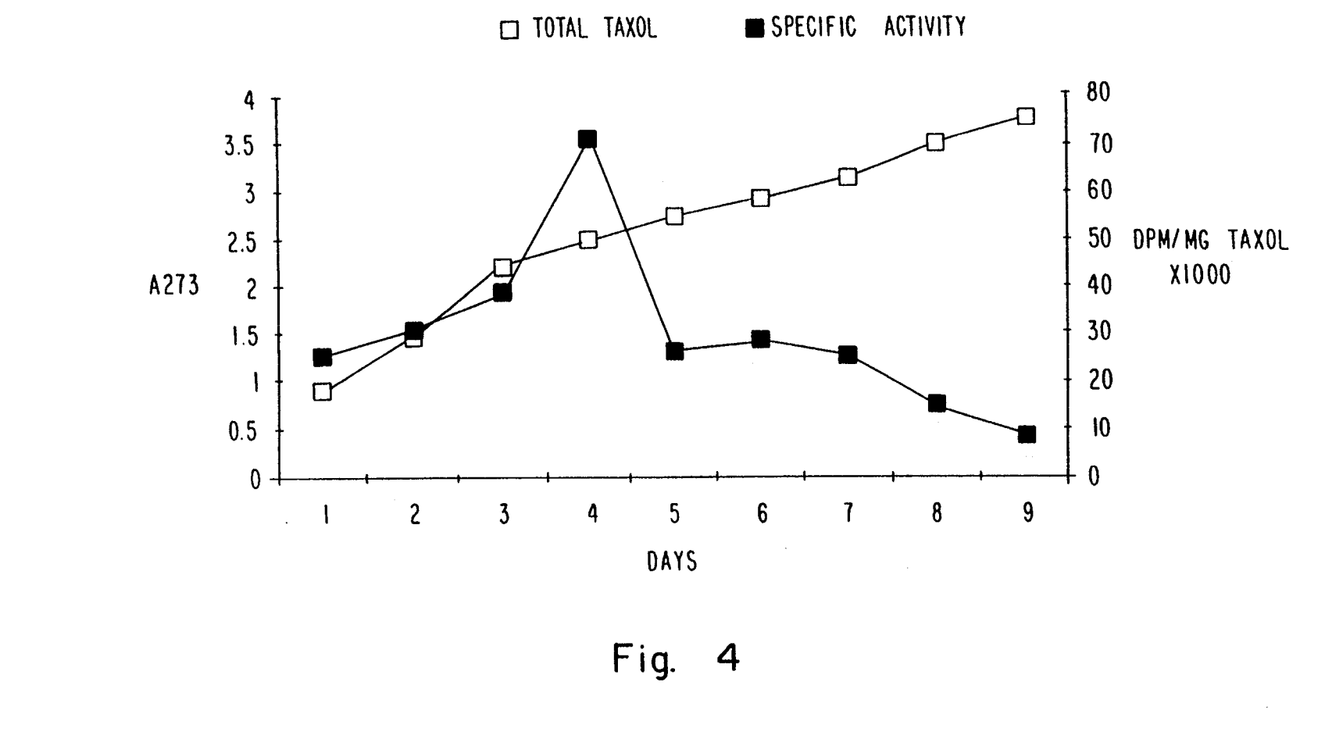
FIG. 4 is a graph showing the cumulative production of taxol wherein, the $Y_2$ axis is a plot of the specific radioactivity in taxol as a function of time (days)

The specific activity of the taxol increased sharply up to days three to four and then tapered off, probably as a result of some limiting factors, as shown in FIG. 4.

The amount of taxol recovered on a dry weight basis was three to four times that which could be extracted from a comparable weight of yew inner bark. For example, 2.5 mg was recovered from the reaction whereas only 0.6 mg could be extracted from 10 grams of fresh inner bark. The identity of taxol was made using FAB mass spec—M+1=854, FIG. 5 and NMR of FIG. 6.

FIG. 3 shows the cumulative production of taxol A273 and the cumulative production of radiolabelled taxol during a nine day incubation period of the yew bark reactor. The label as indicated above, was NaAc-1-$^{14}$C(15 µCi) which was supplied in the fresh reactor solution daily. At least 20 ml of reactor solution were recovered daily and the taxol isolated, quantitatively determined and radioactivity measured. Fresh solution (reactor) was then added to the reactor. FIG. 4 is the same as FIG. 3, except that the Y axis is a plot of the specific radioactivity in taxol as a function of time (days).

Figure 5:
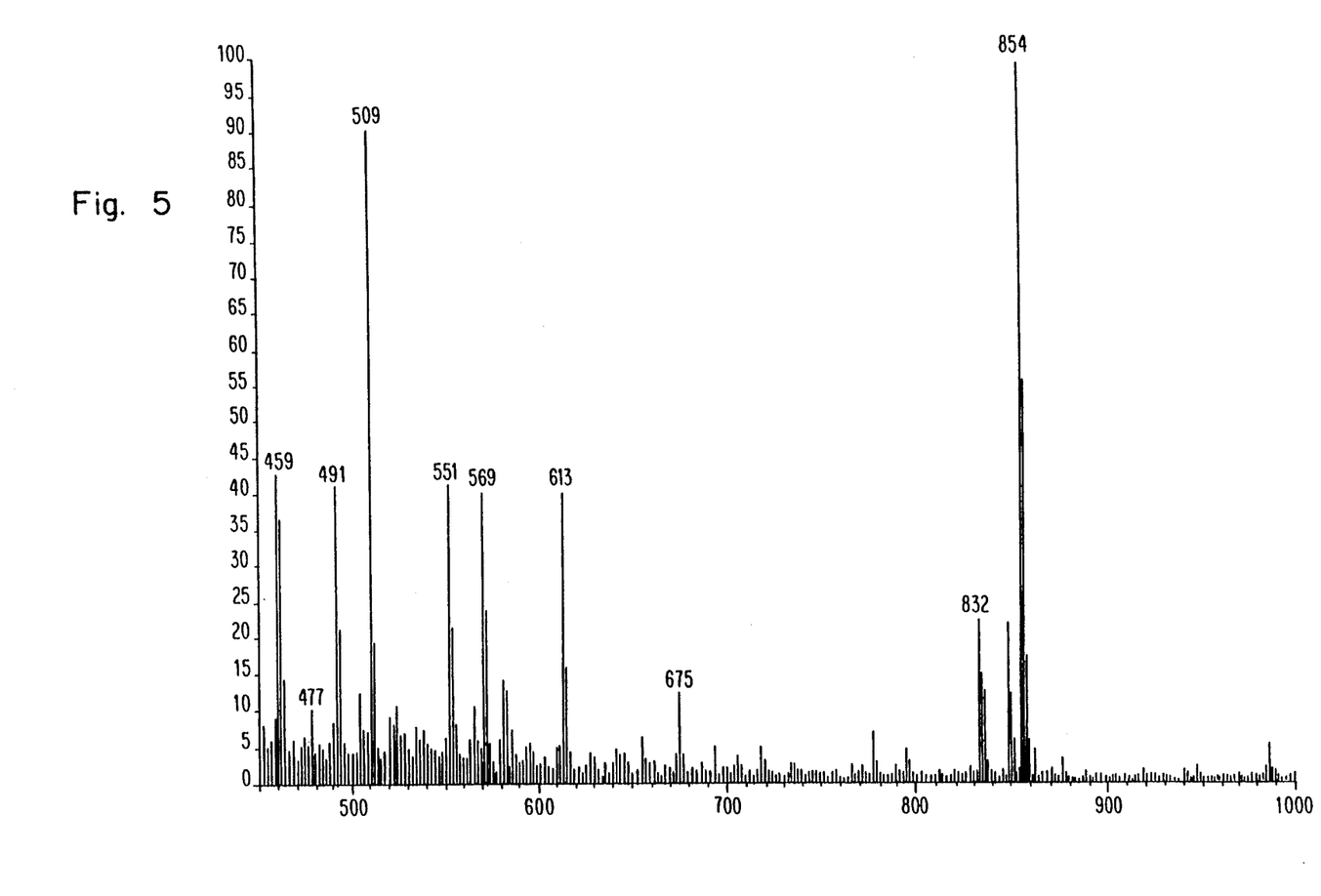
FIG. 5 is a mass spectrometer scan on the taxol isolated from the reactor.
Figure 6:
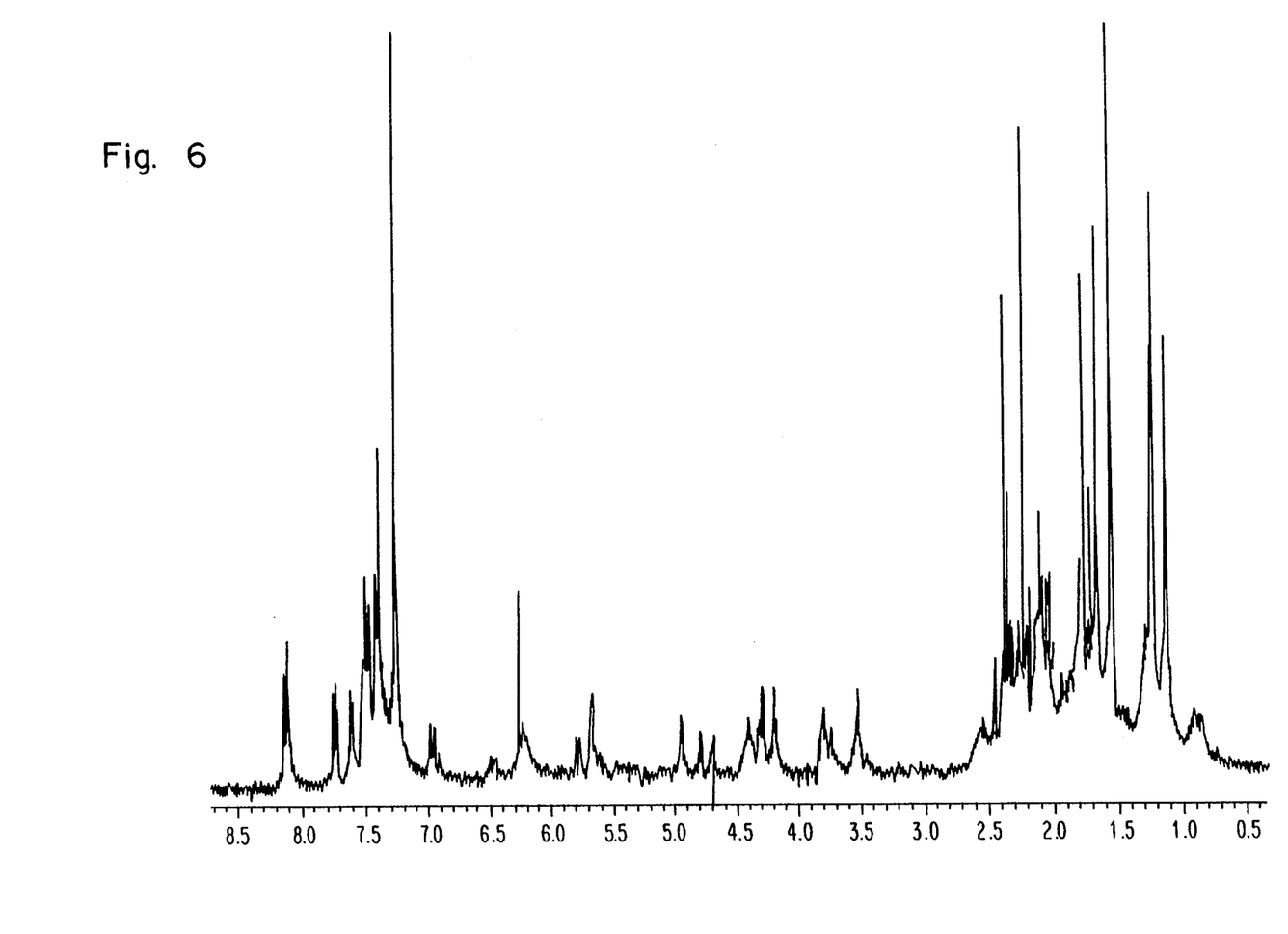
FIG. 6 is a graph showing the NMR of taxol isolated from the reactor.

FIGS. 5 and 6 are FAB mass specs of taxol from the reactor and NMR of taxol from the reactor, respectively. FIG. 6 shows that the NMR of taxol isolated from the yew bark reactor is identical in all respects to standard taxol produced from other sources.

Under the conditions of the reactor of this experiment, it was noted that the reactor solution remained clear each day which suggests minimum bacterial, yeast or fungal contamination. The bark pieces remained white in the reactor and did not turn yellow or brown. No fungal growth was noted on the yew bark species.

The reactor can be optimized for longer periods of sustained taxol production by optimizing the concentration of amino acids, energy sources such as sugar, vitamins and minerals and use of other *Taxus* SP components. Also, an aqueous extract of the Yew tree may be used in the reactor solution or in a facsimile thereof.

EXAMPLE 2

Proving Synthesis with a Labelled Taxol Product

The exact distribution of the $^{14}$C labelling in taxol is best exemplified by an experiment in which Na-acetate-1-$^{13}$C was administered to inner bark pieces. Forty grams of pieces were used and incubated with 0.5 g of Na-acetate-1-$^{13}$C (96 atom % excess). The reactor was incubated for 3 days, then 1.5 mg of taxol was isolated. The taxol present was determined by FAB mass spec—M+1=854 and by proton NMR as shown in the following Table 2. Since C is a stable isotope, it can best be measured by $^{13}$C NMR and enrichment in each carbon atom determined. Those carbons having a ratio better than 1.0 or 1.1 are considered enriched with $^{13}$C. The carbonyl carbons of the acetate groups were the most enriched; however, was distributed throughout the molecule. Considering there is little or no "isotope effect", the pattern of distribution for $^{14}$C in the molecule is likely to be identical to that of $^{13}$C (see Table 1). Thus, labelled acetate ($^{14}$C or $^{13}$C) is an effective compound to administer to the yew reactor in order to acquire nearly uniformly labelled taxol. Some carbons are not labelled since only acetate-1-$^{14}$C or $^{13}$C was used.

TABLE 2

Pattern of $^{13}C$ Distribution in Taxol Derived from Acetate-1-$^{13}C$ in Pacific Yew (inner bark).

Relative Peak Intensity

| Chemical Shift | Std Taxol | $^{13}C$ Derived | Ratio | |
|---|---|---|---|---|
| 204.0 | 1.8 | 2.7 | 1.5 | |
| 173.0 | 2.5 | 2.5 | 1.0 | |
| 171.8 | 1.1 | 2.8 | 2.5 | Carbonyl carbons |
| 170.9 | 1.1 | 3.1 | 2.8 | |
| 166.9 | 2.8 | 2.5 | .89 | |
| 142.3 | 2.0 | 2.3 | 1.15 | Unsaturated carbons |
| 138.5 | 2.3 | 2.1 | .9 | |
| 133.7 | 3.0 | 5.7 | 1.9 | |
| 133.0 | 1.7 | 2.6 | 1.5 | |
| 131.9 | 3.0 | 4.7 | 1.5 | eg., benzene, other double bonds |
| 130.1 | 5.7 | 9.3 | 1.6 | |
| 129.0 | 6.5 | 10.0 | 1.5 | |
| 128.7 | 10.0 | 13.7 | 1.4 | |
| 128.3 | 3.2 | 3.5 | 1.0 | |
| 127.0 | 13.5 | 15.5 | 1.1 | |
| 84.4 | 2.8 | 4.5 | 1.6 | |
| 81.2 | 2.2 | 2.5 | 1.13 | |
| 79.1 | 2.6 | 4.5 | 1.7 | |
| 75.6 | 2.5 | 4.7 | 1.8 | carbons bearing oxygen |
| 75.0 | 2.5 | 4.5 | 1.8 | |
| 73.2 | 2.5 | 4.0 | 1.6 | |
| 72.4 | 3.5 | 4.3 | 1.2 | |
| 72.2 | 2.8 | 4.5 | 1.6 | |
| 58.6 | 2.5 | 3.7 | 1.5 | |
| 55.0 | 3.0 | 4.0 | 1.3 | |
| 45.6 | 2.9 | 4.8 | 1.6 | |
| 43.2 | 2.5 | 3.5 | 1.4 | |
| 35.7 | 2.8 | 4.0 | 1.4 | |
| 35.6 | 3.4 | 4.5 | 1.4 | |
| 26.9 | 4.0 | 5.0 | 1.25 | |
| 22.6 | 3.5 | 5.0 | 1.4 | methyl carbons |
| 21.8 | 2.8 | 4.0 | 1.4 | |
| 20.8 | 2.5 | 5.4 | 2.16 | |
| 14.8 | 2.5 | 5.0 | 2.0 | |
| 9.6 | 3.2 | 5.7 | 2.0 | |

Further examples of yew tissue culture are provided as follows.

EXAMPLE 3

Utilization of Yew Wood Outer Bark in the Reactor

In this example, a reactor as exemplified in FIG. 2 is utilized. The yew wood provided is from basal logs two to three feet in length from the base of a Yew tree one to two meters from ground level. The logs are treated with a solution of 70% ethanol to kill indigenous surface organisms. All knives and lab surfaces are treated with 70% ethanol in preparation for the experiment and sterile gloves are used. In preparing the pieces of the log, the outer bark is removed in 1-2 cm wide and 15-20 cm long pieces, which are then cut into 5 mm×5 mm pieces with sterilized scissors.

The pieces are quickly placed into the reactor solution to prevent drying and oxidation. This process is repeated several times to provide the bark needed for the reactor.

A reactor solution in sterile water is prepared as follows:

1. 10 mM Dithiothreitol;
2. 1 mM Glucose;
3. 1 mM Potassium dihydrogen phosphate and dipotassium hydrogen phosphate to maintain pH at 7.0;
4. 20 mM Phenylalanine and 15 μCi NaAc-1-$^{14}C$; and
5. 0.16 mM Steroid inhibitor, chlorocholine chloride.

In the reactor, there are 0.4 grams of yew bark for each 2 mm of water.

The reactor is started using 10 grams of bark pieces and 30 ml of reactor solution. The reactor is drained daily and quickly replaced with 20 ml of replacement solution having the same composition as described. A sample of 5 ml of each daily reactor solution is extracted with 5 ml of chloroform. The chloroform extract is chromatographed on thin layer chromatography with standard taxol as a reference standard. The band (Rf 0.67) is cut out of the plate and eluted with acetonitrile and taxol estimated at 273 angstroms (E=1700). Radioactivity in this sample is also determined by liquid scintillation counting.

From this experiment, it is clear that de novo production of taxol occurs. The amount of taxol recovered on a dry weight basis is greater than that which could be extracted from a comparable weight of yew outer bark.

Under the conditions of the reactor of this experiment, it is noted that the reactor solution is clear each day which suggests minimum bacterial, yeast or fungal contamination. No fungal growth is noted on the yew bark species.

The reactor can be optimized for longer periods of sustained taxol production by optimizing the concentration of amino acids, energy sources such as sugar, vitamins and minerals. Also, an aqueous extract of the Yew tree may be used in the reactor solution or in a facsimile thereof.

EXAMPLE 4

Using Yew Wood New Growth Tissue in the Reactor

In this example, a reactor as exemplified in FIG. 2 is utilized. The yew wood provided is from basal logs two to three feet in length from the base of a Yew tree one to two meters from ground level. The logs are treated with a solution of 70% ethanol to kill indigenous surface organisms. All knives and lab surfaces are treated with 70% ethanol in preparation for the experiment and sterile gloves .are used. In preparing the pieces of the log, the inner and outer bark are removed. New growth tissue is then removed in 1-2 cm wide and 15-20 cm long pieces, which are then cut into 5 mm×5 mm pieces with sterilized tools.

The pieces are quickly placed into the reactor solution to prevent drying and oxidation. This process is repeated several times to provide the Yew wood tissue needed for the reactor.

A reactor solution in sterile water is prepared as follows:

1. 10 mM Dithiothreitol;
2. 1 mM Glucose;
3. 1 mM Potassium dihydrogen phosphate and dipotassium hydrogen phosphate to maintain pH at 7.0;
4. 20 mM Phenylalanine and 15 μCi NaAc-1-$^{14}C$; and
5. 0.16 mM Steroid inhibitor, chlorocholine chloride.

In the reactor, there are 0.4 grams of yew bark for each 2 mm of water.

The reactor is started using 10 grams of bark pieces and 30 ml of reactor solution. The reactor is drained daily and quickly replaced with 20 ml of replacement solution having the same composition as described. A sample of 5 ml of each daily reactor solution is extracted with 5 ml of chloroform. The chloroform extract is chromatographed on thin layer chromatography with standard taxol as a reference standard. The band (Rf 0.67) is cut out of the plate and eluted with acetonitrile and taxol estimated at 273 angstroms (E=1700). Radioactivity in this sample is also determined by liquid scintillation counting.

From this experiment, it is clear that de novo production of taxol occurs. The amount of taxol recovered on a dry weight basis is greater than that which could be extracted from a comparable weight of yew wood new growth tissue.

EXAMPLE 5

Using Yew Wood Old Growth Tissue in the Reactor

In this example, a reactor as exemplified in FIG. 2 is utilized. The yew wood provided is from basal logs two to three feet in length from the base of a Yew tree one to two meters from ground level. The logs are treated with a solution of 70% ethanol to kill indigenous surface organisms. All knives and lab surfaces are treated with 70% ethanol in preparation for the experiment and sterile gloves are used. In preparing the pieces of the log, the inner and outer bark and the new growth tissue are removed. Old growth tissue is then removed in 1–2 cm wide and 15–20 cm long pieces, which are then cut into 5 mm×5 mm pieces with sterilized tools.

The pieces are quickly placed into the reactor solution to prevent drying and oxidation. This process is repeated several times to provide the Yew wood old growth tissue needed for the reactor.

A reactor solution in sterile water is prepared as follows:
1. 10 mM Dithiothreitol;
2. 1 mM Glucose;
3. 1 mM Potassium dihydrogen phosphate and dipotassium hydrogen phosphate to maintain pH at 7.0;
4. 20 mM Phenylalanine and 15 $\mu$Ci NaAc-1-$^{14}$C; and
5. 0.16 mM Steroid inhibitor, chlorocholine chloride.

In the reactor, there are 0.4 grams of yew bark for each 2 mm of water.

The reactor is started using 10 grams of bark pieces and 30 ml of reactor solution. The reactor is drained daily and quickly replaced with 20 ml of replacement solution having the same composition as described. A sample of 5 ml of each daily reactor solution is extracted with 5 ml of chloroform. The chloroform extract is chromatographed on thin layer chromatography with standard taxol as a reference standard. The band (Rf 0.67) is cut out of the plate and eluted with acetonitrile and taxol estimated at 273 angstroms (E=1700). Radioactivity in this sample is also determined by liquid scintillation counting.

From this experiment, it is clear that de novo production of taxol occurs. The amount of taxol recovered on a dry weight basis is greater than that which could be extracted from a comparable weight of yew wood old growth tissue.

EXAMPLE 6

Using Yew Wood Large Branch Tissue in the Reactor

In this example, a reactor as exemplified in FIG. 2 is utilized. The yew wood provided is from large branches from the upper portions of a Yew tree several meters from ground level. The branches are treated with a solution of 70% ethanol to kill indigenous surface organisms. All knives and lab surfaces are treated with 70% ethanol in preparation for the experiment and sterile gloves are used. In preparing the pieces of the branches the inner and outer bark and the remainder of the branch tissue are used. Branch tissue is cut into 5 mm×5 mm pieces with sterilized tools.

The pieces are quickly placed into the reactor solution to prevent drying and oxidation. This process is repeated several times to provide the Yew wood large branch tissue needed for the reactor.

A reactor solution in sterile water is prepared as follows:
1. 10 mM Dithiothreitol;
2. 1 mM Glucose;
3. 1 mM Potassium dihydrogen phosphate and dipotassium hydrogen phosphate to maintain pH at 7.0;
4. 20 mM Phenylalanine and 15 $\mu$Ci NaAc-1-$^{14}$C; and
5. 0.16 mM Steroid inhibitor, chlorocholine chloride.

In the reactor, there are 0.4 grams of yew bark for each 2 mm of water.

The reactor is started using 10 grams of bark pieces and 30 ml of reactor solution. The reactor is drained daily and quickly replaced with 20 ml of replacement solution having the same composition as described. A sample of 5 ml of each daily reactor solution is extracted with 5 ml of chloroform. The chloroform extract is chromatographed on thin layer chromatography with standard taxol as a reference standard. The band (Rf 0.67) is cut out of the plate and eluted with acetonitrile and taxol estimated at 273 angstroms (E=1700). Radioactivity in this sample is also determined by liquid scintillation counting.

From this experiment, it is clear that de novo production of taxol occurs. The amount of taxol recovered on a dry weight basis is greater than that which could be extracted from a comparable weight of yew wood large branch tissue.

Under the conditions of the reactor of this experiment, it is noted that the reactor solution is clear each day which suggests minimum bacterial, yeast or fungal contamination. No fungal growth is noted on the yew large branch tissue species.

EXAMPLE 7

Using Yew Wood Small Branch Tissue in the Reactor

In this example, a reactor as exemplified in FIG. 2 is utilized. The yew wood provided is from small branches and twigs from branches of a Yew tree. The branches are treated with a solution of 70% ethanol to kill indigenous surface organisms. All knives and lab surfaces are treated with 70% ethanol in preparation for the experiment and sterile gloves are used. In preparing the pieces of the branches and twigs the inner and outer bark and the remainder of the branch tissue are used. Branch tissue and twigs are cut into 5 mm×5 mm pieces with sterilized tools.

The pieces are quickly placed into the reactor solution to prevent drying and oxidation. This process is repeated several times to provide the Yew wood small branch and twig tissue needed for the reactor.

A reactor solution in sterile water is prepared as follows:
1. 10 mM Dithiothreitol;
2. 1 mM Glucose;
3. 1 mM Potassium dihydrogen phosphate and dipotassium hydrogen phosphate to maintain pH at 7.0;
4. 20 mM Phenylalanine and 15 $\mu$Ci NaAc-1-$^{14}$C; and
5. 0.16 mM Steroid inhibitor, chlorocholine chloride.

In the reactor, there are 0.4 grams of yew bark for each 2 mm of water.

The reactor is started using 10 grams of bark pieces and 30 ml of reactor solution. The reactor is drained daily and quickly replaced with 20 ml of replacement solution having the same composition as described. A sample of 5 ml of each daily reactor solution is extracted with 5 ml of chloroform. The chloroform extract is chromatographed on thin layer chromatography with standard taxol as a reference standard. The band (Rf 0.67) is cut out of the plate and eluted with acetonitrile and taxol estimated at 273 angstroms (E=1700). Radioactivity in this sample is also determined by liquid scintillation counting.

From this experiment, it is clear that de novo production of taxol occurs. The amount of taxol recovered on a dry weight basis is greater than that which could be extracted from a comparable weight of yew wood small branch and twig tissue. The reactor solution is clear each day which suggests minimum bacterial, yeast or fungal contamination. No fungal growth is noted on the yew small branch and twig tissue species.

EXAMPLE 8

Using Yew Needles in the Reactor

In this example, a reactor as exemplified in FIG. 2 is utilized. The yew needles are obtained from the yew tree. The needles are treated with a solution of 70% ethanol to kill indigenous surface organisms. All knives and lab surfaces are treated with 70% ethanol in preparation for the experiment and sterile gloves are used. In preparing the pieces of needles, the needles are chopped into small pieces with sterilized scissors.

The pieces are quickly placed into the reactor solution to prevent drying and oxidation. This process is repeated several times to provide the Yew needles needed for the reactor.

A reactor solution in sterile water is prepared as follows:

1. 10 mM Dithiothreitol;
2. 1 mM Glucose;
3. 1 mM Potassium dihydrogen phosphate and dipotassium hydrogen phosphate to maintain pH at 7.0;
4. 20 mM Phenylalanine and 15 $\mu$Ci NaAc-1-$^{14}$C; and
5. 0.16 mM Steroid inhibitor, chlorocholine chloride.

In the reactor, there are 0.4 grams of yew bark for each 2 mm of water.

The reactor is started using 10 grams of bark pieces and 30 ml of reactor solution. The reactor is drained daily and quickly replaced with 20 ml of replacement solution having the same composition as described. A sample of 5 ml of each daily reactor solution is extracted with 5 ml of chloroform. The chloroform extract is chromatographed on thin layer chromatography with standard taxol as a reference standard. The band (Rf 0.67) is cut out of the plate and eluted with acetonitrile and taxol estimated at 273 angstroms (E=1700). Radioactivity in this sample is also determined by liquid scintillation counting.

From this experiment, it is clear that de novo production of taxol occurs. The amount of taxol recovered on a dry weight basis is greater than that which could be extracted from a comparable weight of yew needles. The reactor solution is clear each day which suggests minimum bacterial, yeast or fungal contamination. No fungal growth is noted on the yew needles.

EXAMPLE 9

Using Yew Wood Root Tissue in the Reactor

In this example, a reactor as exemplified in FIG. 2 is utilized. The yew wood provided is from the roots of a Yew tree. The roots are washed with sterile water and then treated with a solution of 70% ethanol to kill indigenous surface organisms. All knives and lab surfaces are treated with 70% ethanol in preparation for the experiment and sterile gloves are used. In preparing the pieces of the roots the outer bark of the roots are removed and the inner bark tissue is used. The root inner bark tissue is removed from the root and is cut into 5 mm×5 mm pieces with sterilized scissors.

The pieces are quickly placed into the reactor solution to prevent drying and oxidation. This process is repeated several times to provide the Yew root inner bark tissue needed for the reactor.

A reactor solution in sterile water is prepared as follows:

1. 10 mM Dithiothreitol;
2. 1 mM Glucose;
3. 1 mM Potassium dihydrogen phosphate and dipotassium hydrogen phosphate to maintain pH at 7.0;
4. 20 mM Phenylalanine and 15 $\mu$Ci NaAc-1-$^{14}$C; and
5. 0.16 mM Steroid inhibitor, chlorocholine chloride.

In the reactor, there are 0.4 grams of yew bark for each 2 mm of water.

The reactor is started using 10 grams of bark pieces and 30 ml of reactor solution. The reactor is drained daily and quickly replaced with 20 ml of replacement solution having the same composition as described. A sample of 5 ml of each daily reactor solution is extracted with 5 ml of chloroform. The chloroform extract is chromatographed on thin layer chromatography with standard taxol as a reference standard. The band (Rf 0.67) is cut out of the plate and eluted with acetonitrile and taxol estimated at 273 angstroms (E=1700). Radioactivity in this sample is also determined by liquid scintillation counting.

From this experiment, it is clear that de novo production of taxol occurs. The amount of taxol recovered on a dry weight basis is greater than that which could be extracted from a comparable weight of yew root inner bark tissue. The reactor solution is clear each day which suggests minimum bacterial, yeast or fungal contamination. No fungal growth is noted on the yew root tissue species.

The foregoing description of the specific embodiments will so fully reveal the general nature of the invention that others can, by applying current knowledge, readily modify and/or adapt for various applications such specific embodiments without departing from the generic concept and therefore such adaptations are intended to be comprehended within the meaning and range of equivalents of the disclosed embodiments. It is to be understood that the phraseology or terminology employed herein is for the purpose of description only and not of limitation.

What is claimed is:

1. A method for the production of taxol from a Yew tree which comprises:
   (a) providing a taxol source from a portion of a Yew tree;
   (b) contacting said portion of Yew tree with an aqueous reactor solution comprising a taxol precursor comprising phenylalanine and a steroid inhibitor comprising chlorocholine chloride; said solution being maintained at a pH of about 6.0 to 8.0 at a temperature of about 25°–30° C. and under a reducing environment; and (c) maintaining contact of said taxol source with said reactor solution for a sufficient time to produce taxol.

2. A method according to claim 1, wherein the reducing environment is provided by a reducing agent.

3. A method according to claim 1, wherein the reactor solution contains an energy source.

4. A method according to claim 1, wherein the reactor solution contains a buffering reagent.

5. A method according to claim 1, wherein the reactor solution contains vitamins and minerals.

6. A method according to claim 1, wherein a $^{14}C$, $^{13}C$, $^{3}H$ or $^{15}N$ radioactivity precursor is contained in said reactor solution.

7. A method according to claim 1, wherein the Yew tree portion is freshly cut prior to introduction into the reactor.

8. A method according to claim 3, wherein the Yew tree portion is sterilized prior to introduction into the reactor.

9. A method according to claim 8, wherein sterilization of the Yew tree portion is effected by contact with an aqueous alcoholic solution.

10. A method according to claim 1, wherein the Yew tree portion is selected from the group consisting of:
trunk inner bark, branch or twig inner bark,
trunk outer bark, branch or twig outer bark,
new growth tissue, old growth tissue, large branch mixed tissue, small branch mixed tissue, needle tissue, and root tissue.

11. A method according to claim 1, wherein the portion of the Yew tree is obtained from the lower 20% of the trunk of the tree.

12. A method according to claim 10, wherein the Yew tree portion comprises the inner bark of the Yew tree.

13. A method according to claim 2, wherein the reducing agent is dithiothreitol, ascorbic acid, mercaptoethanol, or mixtures thereof.

14. A method according to claim 3, wherein the energy source is a sugar.

15. A method according to claim 1, wherein the taxol precursor further comprises a chemical compound which contains acyl radicals or other amino acids.

16. A method according to claim 1, wherein the taxol precursor further comprises acyl radicals or corresponding acyl halides, esters or salts, amino acids or lactones.

17. A method according to claim 1, wherein the taxol precursor further comprises acetic acid or an ester thereof, or another amino acid, or benzoic acid or an ester or salt thereof.

18. A method according to claim 15, wherein the taxol precursor further comprises acetic acid or acetate.

19. A method according to claim 1, wherein the steroid inhibitor further comprises a compound selected from the group consisting of a fungal elicitor, gibberellic acid $A_3$ and mixtures thereof 20. A method according to claim 1, wherein the taxol precursor is radiolabelled with $^{14}C$, $^{13}C$, $^{3}H$ or $^{15}N$.

21. A continuous process for the production of taxol from a Yew tree which comprises:
(a) providing a taxol source from a portion of Yew tree;
(b) contacting said portion of Yew tree with an aqueous reactor solution comprising:
(1) a reducing agent,
(2) an energy source,
(3) a taxol precursor comprising phenylalanine and
(4) asteroid inhibitor comprising chlorocholine chloride;
said solution being maintained at a pH of about 6.5 to 7.0 and a temperature of 25°–30° C.; and
(c) maintaining contact of said few portions with said reactor solution at said pH and temperature for a sufficient time to produce taxol;
(d) periodically removing at least a portion of said reactor solution and replacing with fresh reactor solution; and
(e) recovering taxol from said reactor solution.

22. A process for the production of taxol from a Yew tree which comprises:
(a) providing a taxol source from a portion of a Yew tree;
(b) contacting said portion of Yew tree with an aqueous reactor solution comprising:
(1) a reducing agent selected from the group consisting of dithiothreitol, ascorbic acid and mixtures thereof;
(2) an energy source comprising a sugar;
(3) a buffer to maintain pH at 6.5 to 7.0;
(4) a taxol precursor comprising an acyl compound or amino acid;
(5) a steroid inhibitor comprising chlorocholine chloride;
said solution being maintained at a pH of about 6.5 to 7.0 and a temperature of 25°–30° C.;
(c) maintaining contact of said yew portions with said reactor solution at said pH and temperature for a sufficient time to produce taxol;
(d) recovering taxol from said reactor solution.

* * * * *

UNITED STATES PATENT AND TRADEMARK OFFICE
CERTIFICATE OF CORRECTION

PATENT NO. : 5,445,809
DATED : August 29, 1995
INVENTOR(S) : Gary A. Strobel et al It is certified that error appears in the above-indentified patent and that said Letters Patent is hereby corrected as shown below:

Column 1, after the title of the invention, insert the following:

-- This invention was made with support under grant number CHE-9206803 awarded by the National Science Foundation.--

Signed and Sealed this

Twentieth Day of August, 1996

Attest:

BRUCE LEHMAN

Attesting Officer        Commissioner of Patents and Trademarks